(12) United States Patent
Sheehan et al.

(10) Patent No.: US 12,109,065 B2
(45) Date of Patent: Oct. 8, 2024

(54) DEVICES, SYSTEMS, AND METHODS FOR VESSEL ASSESSMENT

(71) Applicant: PHILIPS IMAGE GUIDED THERAPY CORPORATION, San Diego, CA (US)

(72) Inventors: David M. Sheehan, Poway, CA (US); Bernhard Sturm, Davis, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 18/242,127

(22) Filed: Sep. 5, 2023

(65) Prior Publication Data
US 2023/0404525 A1    Dec. 21, 2023

Related U.S. Application Data

(63) Continuation of application No. 17/469,195, filed on Sep. 8, 2021, now Pat. No. 11,744,544, which is a
(Continued)

(51) Int. Cl.
*A61B 8/12*    (2006.01)
*A61B 5/00*    (2006.01)
(Continued)

(52) U.S. Cl.
CPC .............. *A61B 8/12* (2013.01); *A61B 5/0095* (2013.01); *A61B 5/02007* (2013.01);
(Continued)

(58) Field of Classification Search
CPC ............ A61B 2090/364; A61B 5/0035; A61B 5/0066; A61B 5/0095; A61B 5/02007;
(Continued)

(56) References Cited

U.S. PATENT DOCUMENTS 5,357,550 A    10/1994    Asahina
6,909,792 B1    6/2005    Carrott
(Continued)

FOREIGN PATENT DOCUMENTS

JP    2012005636 A    1/2012
JP    05390180 B2    1/2014
(Continued)

*Primary Examiner* — Mark D Remaly

(57) ABSTRACT

Devices, systems, and methods for visually depicting a vessel and evaluating a physiological condition of the vessel are disclosed. One embodiment includes obtaining, at a first time, a first image of the vessel, the image being in a first medical modality, and obtaining, at a second time subsequent to the first time, a second image of the vessel, the image being in the first medical modality. The method also includes spatially co-registering the first and second images and outputting a visual representation of the co-registered first and second images on a display. Further, the method includes determining a physiological difference between the vessel at the first time and the vessel at the second time based on the co-registered first and second images, and evaluating the physiological condition of the vessel of the patient based on the determined physiological difference.

17 Claims, 11 Drawing Sheets

Related U.S. Application Data continuation of application No. 14/702,940, filed on May 4, 2015, now abandoned.

(60) Provisional application No. 61/989,219, filed on May 6, 2014.

(51) Int. Cl.

| | |
|---|---|
| *A61B 5/02* | (2006.01) |
| *A61B 5/0215* | (2006.01) |
| *A61B 6/00* | (2006.01) |
| *A61B 6/03* | (2006.01) |
| *A61B 6/46* | (2024.01) |
| *A61B 6/50* | (2024.01) |
| *A61B 8/00* | (2006.01) |
| *A61B 8/08* | (2006.01) |
| *G01R 33/34* | (2006.01) |
| *G01R 33/48* | (2006.01) |
| *G06T 7/00* | (2017.01) |
| *A61B 5/055* | (2006.01) |
| *A61B 5/107* | (2006.01) |
| *A61B 90/00* | (2016.01) |
| *A61F 2/82* | (2013.01) |
| *G01R 33/28* | (2006.01) |
| *G01R 33/563* | (2006.01) |

(52) U.S. Cl.
CPC .......... *A61B 5/0215* (2013.01); *A61B 5/4848* (2013.01); *A61B 5/7425* (2013.01); *A61B 6/032* (2013.01); *A61B 6/037* (2013.01); *A61B 6/4417* (2013.01); *A61B 6/463* (2013.01); *A61B 6/504* (2013.01); *A61B 6/5247* (2013.01); *A61B 8/0883* (2013.01); *A61B 8/0891* (2013.01); *A61B 8/4416* (2013.01); *G01R 33/34084* (2013.01); *G01R 33/48* (2013.01); *G06T 7/0016* (2013.01); *A61B 5/0035* (2013.01); *A61B 5/0066* (2013.01); *A61B 5/055* (2013.01); *A61B 5/1075* (2013.01); *A61B 5/1076* (2013.01); *A61B 5/1079* (2013.01); *A61B 2090/364* (2016.02); *A61F 2/82* (2013.01); *G01R 33/285* (2013.01); *G01R 33/4808* (2013.01); *G01R 33/5635* (2013.01); *G06T 2207/30104* (2013.01)

(58) Field of Classification Search
CPC ..... A61B 5/0215; A61B 5/055; A61B 5/1075; A61B 5/1076; A61B 5/1079; A61B 5/4848; A61B 5/7425; A61B 6/032; A61B 6/037; A61B 6/4417; A61B 6/463; A61B 6/504; A61B 6/5247; A61B 8/0883; A61B 8/0891; A61B 8/12; A61B 8/4416; A61F 2/82; G01R 33/285; G01R 33/34084; G01R 33/48; G01R 33/4808; G01R 33/5635; G06T 2207/30104; G06T 7/0016

See application file for complete search history.

(56) References Cited

U.S. PATENT DOCUMENTS

| | | |
|---|---|---|
| 7,031,504 B1 | 4/2006 | Argiro |
| 7,356,367 B2 | 4/2008 | Liang |
| 7,492,931 B2 | 2/2009 | Sabol |
| 7,930,014 B2 | 4/2011 | Huennekens |
| 8,594,402 B2 | 11/2013 | Shirasaka |
| 9,107,639 B2 | 8/2015 | Arvidsson |
| 9,730,613 B2 | 8/2017 | Stigall |
| 2003/0208116 A1 | 11/2003 | Liang |
| 2004/0133094 A1 | 7/2004 | Becker |
| 2005/0113961 A1 | 5/2005 | Sabol |
| 2006/0241465 A1 | 10/2006 | Huennekens |
| 2006/0241478 A1 | 10/2006 | Lewis |
| 2007/0116342 A1 | 5/2007 | Zarkh |
| 2007/0232896 A1 | 10/2007 | Gilboa |
| 2007/0244393 A1 | 10/2007 | Oshiki |
| 2007/0248253 A1 | 10/2007 | Manzke |
| 2008/0221440 A1 | 9/2008 | Iddan |
| 2008/0221442 A1 | 9/2008 | Tolkowski |
| 2009/0281418 A1 | 11/2009 | Ruijters |
| 2010/0160773 A1 | 6/2010 | Cohen |
| 2011/0064285 A1 | 3/2011 | Chen |
| 2012/0004537 A1 | 1/2012 | Tolkowsky |
| 2012/0236032 A1 | 9/2012 | Arvidsson |
| 2012/0310081 A1 | 12/2012 | Adler |
| 2013/0046190 A1 | 2/2013 | Davies |
| 2013/0208957 A1 | 8/2013 | Wiesner |
| 2014/0187920 A1 | 7/2014 | Millet |
| 2014/0276684 A1 | 9/2014 | Huennekens |
| 2015/0025330 A1 | 1/2015 | Davies |
| 2015/0182192 A1 | 7/2015 | Kaneko |

FOREIGN PATENT DOCUMENTS

| | | |
|---|---|---|
| KR | 2006108000 A | 10/2006 |
| WO | 2010058398 A2 | 5/2010 |
| WO | 2012001412 A1 | 2/2012 |
| WO | 2012126070 A1 | 9/2012 |
| WO | 2013035005 A1 | 3/2013 |
| WO | 2014001980 A1 | 1/2014 |

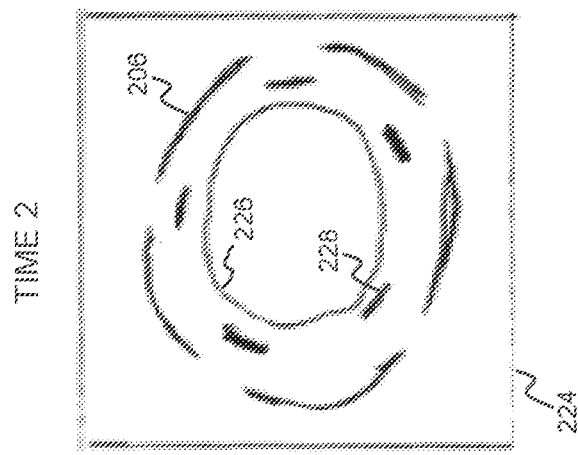
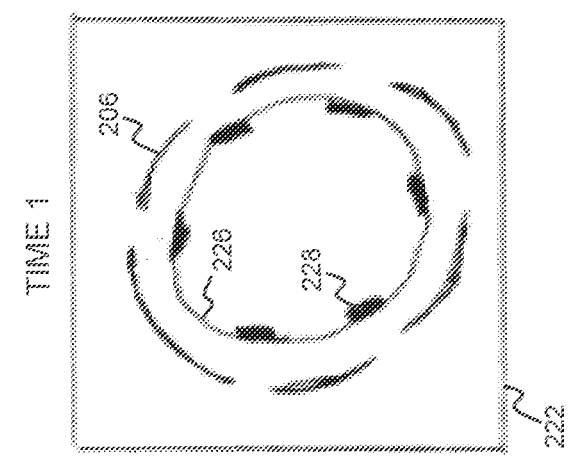
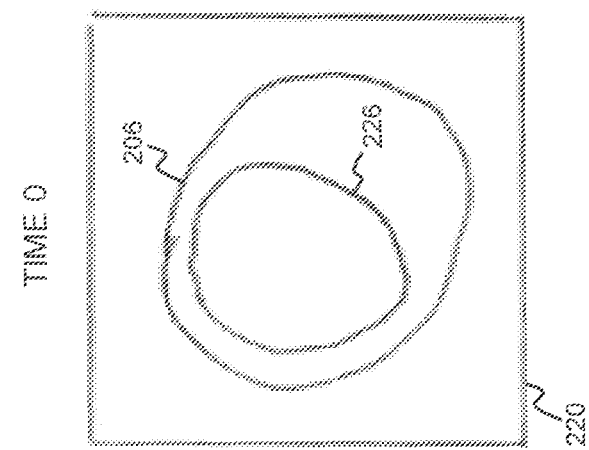
Fig. 7

DEVICES, SYSTEMS, AND METHODS FOR VESSEL ASSESSMENT

CROSS REFERENCE TO RELATED APPLICATIONS

The present application is a continuation of U.S. patent application Ser. No. 17/469,195, filed Sep. 8, 2021, now U.S. Pat. No. 11,744,544, which is a continuation of U.S. patent application Ser. No. 14/702,940, filed May 4, 2015, which claims priority to and the benefit of U.S. Provisional Patent Application No. 61/989,219, filed May 6, 2014, each of which is hereby incorporated by reference in its entirety.

TECHNICAL FIELD

The present disclosure relates generally to the assessment of vessels and, in particular, the assessment of physiological changes in vessels over time. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include percutaneous coronary intervention (PCI or angioplasty), stenting, or coronary artery bypass graft (CABG) surgery. As with all medical procedures, certain risks are associated with PCI, stenting, and CABG procedures. In order for a surgeon to make a better-informed decision regarding treatment options, additional information about the risk and likelihood of success associated with the treatment options is needed.

Additionally, numerical calculations such as FFR are used to track the effectiveness of an intravascular procedure, such as the insertion of a stent in a vessel. Typically, to evaluate the effectiveness of an intravascular procedure, a practitioner will conduct a longitudinal study over a time period that encompasses the procedure. For example, FFR calculations may be performed before and after an intravascular procedure to track the improvement of the patient. However, such numerical-based longitudinal studies are less than ideal because they require a practitioner to perform mental estimations about any physiological changes in the vessel.

Accordingly, there remains a need for improved devices, systems, and methods for assessing physiological changes in a vessel over time.

SUMMARY

Embodiments of the present disclosure are configured to assess physiological changes in a vessel over time. In some particular embodiments, the devices, systems, and methods of the present disclosure are configured to provide co-registered visual depictions of a vessel at different points in time that allow assessment of changes in the vessel. Further, in some embodiments, the devices, systems, and methods of the present disclosure are configured to provide co-registered visual depictions of a vessel in different imaging modalities that facilitate assessment of the vessel over a time period.

In one embodiment, a method of evaluating a vessel of a patient is provided. The method includes obtaining, at a first time, a first graphical diagnostic measurement of the vessel of the patient, the first graphical diagnostic measurement being in a first medical modality, and obtaining, at a second time subsequent to the first time, a second graphical diagnostic measurement of the vessel, the graphical diagnostic measurement being in the first medical modality. The method also includes spatially co-registering the first and second graphical diagnostic measurements, and outputting a visual representation of the co-registered first and second graphical diagnostic measurements on a display. Additionally, the method includes determining a physiological difference between the vessel at the first time and the vessel at the second time based on the co-registered first and second graphical diagnostic measurements, and evaluating the physiological condition of the vessel of the patient based on the determined physiological difference.

In another embodiment, a second method of evaluating a vessel of a patient is disclosed. The method includes obtaining, at a first time, a first graphical diagnostic measurement of the vessel, the first graphical diagnostic measurement being in a first medical imaging modality, and obtaining, at the first time, a second graphical diagnostic measurement of the vessel, the second graphical diagnostic measurement being in a second medical imaging modality different than the first medical imaging modality. The method also includes obtaining, at a second time, a third graphical diagnostic measurement of the vessel, the third graphical diagnostic measurement being in the first medical imaging modality, and obtaining, at the second time, a fourth graphical diagnostic measurement of the vessel, the fourth graphical diagnostic measurement being in the second medical imaging modality. Additionally, the method includes spatially co-registering the first and third graphical diagnostic measurements, spatially co-registering the second and fourth graphical diagnostic measurements, and spatially and temporally co-registering the first and second graphical diagnostic measurements. The method further includes outputting a visual representation of the co-registered first, second, third, and fourth graphical diagnostic measurements on a display, and determining a physiological difference between the vessel at the first time and the vessel at the second time based on at least one of the co-registered first and third graphical diagnostic measurements and the co-registered second and fourth graphical diagnostic measurements. The method also includes evaluating the physiological condition of the vessel based on the determined physiological difference.

In yet another embodiment, a system of evaluating a vessel of a patient is disclosed. The system includes an instrument configured to obtain graphical diagnostic measurements of the vessel of the patient and a processing system in communication with the first instrument. The processing unit is configured to obtain, at a first time, a first graphical diagnostic measurement of the vessel from the instrument, the first graphical diagnostic measurement being in a first medical modality and obtain, at a second time subsequent to the first time, a second graphical diagnostic measurement of the vessel from the instrument, the graphical diagnostic measurement being in the first medical modality. The processing unit is also configured to spatially co-register the first and second graphical diagnostic measurements and output a visual representation of the co-registered first and second graphical diagnostic measurements on a display. Additionally, the processing unit is configured to determine a physiological difference between the vessel at the first time and the vessel at the second time based on the co-registered first and second graphical diagnostic measurements, and evaluate the physiological condition of the vessel of the patient based on the determined physiological difference Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 5-8 are stylized images of a portion of a patient's vasculature according to embodiments of the present disclosure.

DETAILED DESCRIPTION

Figure 1:
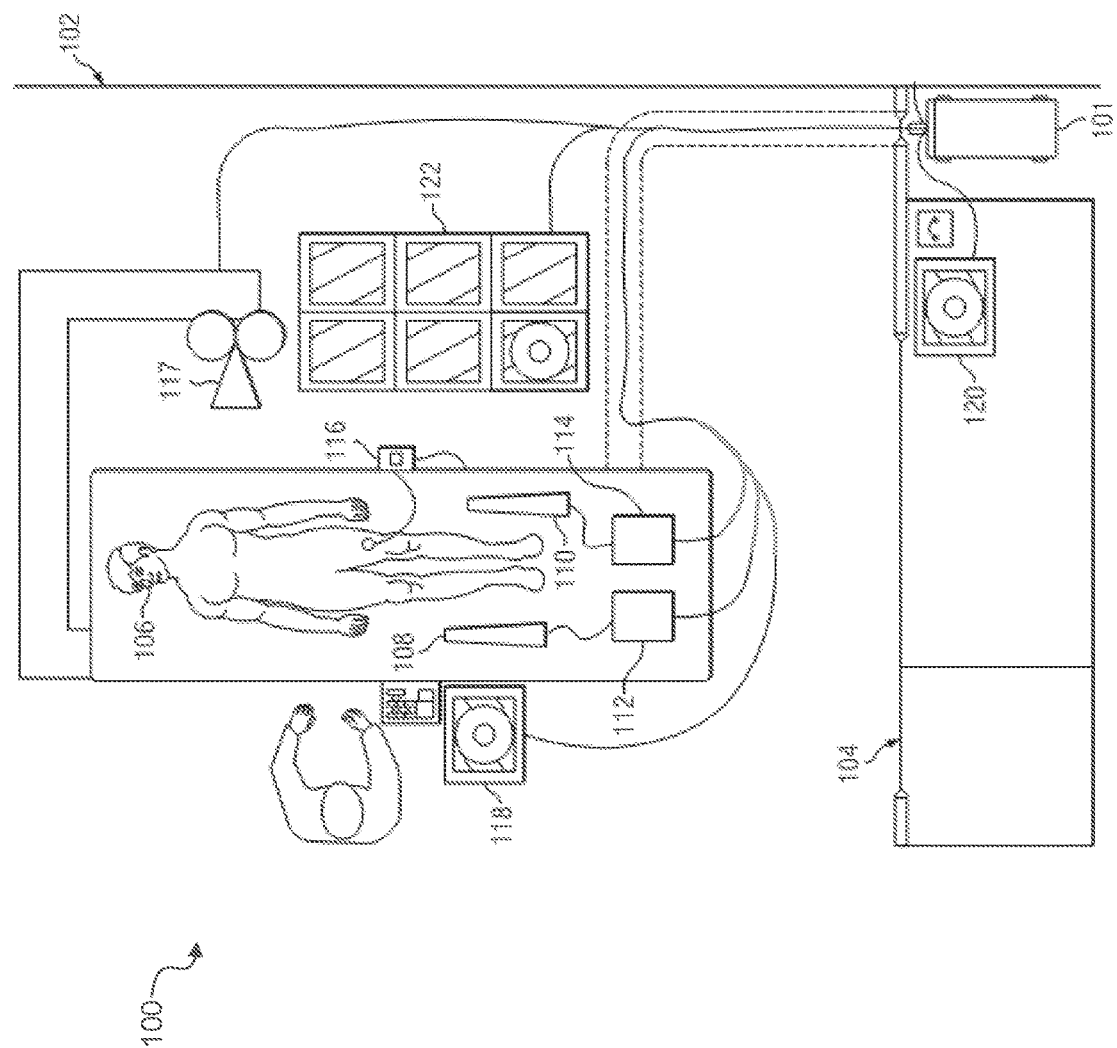
FIG. 1 is a schematic drawing depicting a medical system including a multi-modality processing system according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical system 100 including a multi-modality processing system 101 according to one embodiment of the present disclosure. In general, the medical system 100 provides for coherent integration and consolidation of multiple forms of acquisition and processing elements designed to be sensitive to a variety of methods used to acquire and interpret human biological physiology and morphological information. More specifically, in system 100, the multi-modality processing system 101 is an integrated device for the acquisition, control, interpretation, and display of multi-modality medical data. In one embodiment, the processing system 101 is a computer system with the hardware and software to acquire, process, and display multi-modality medical data, but, in other embodiments, the processing system 101 may be any other type of computing system operable to process medical sensing data. In the embodiments in which processing system 101 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), one or more video controllers such as a graphics processing unit (GPU), and a network communication device such as an Ethernet controller. In that regard, in some particular instances the processing system 101 is programmed to execute steps associated with the data acquisition, analysis, and co-registration described herein. Accordingly, it is understood that any steps related to data acquisition, data processing, instrument control, and/or other processing or control aspects of the present disclosure may be implemented by the processing system using corresponding instructions stored on or in a non-transitory computer readable medium accessible by the processing system. In some instances, the processing system 101 is a console computing device. In some particular instances, the processing system 101 is similar to the s5™ Imaging System, the s5i™ Imaging System, or other imaging systems available from Volcano Corporation. In some instances, the processing system 101 is portable (e.g., handheld, on a rolling cart, etc.). Further, it is understood that in some instances processing system 101 comprises a plurality of computing devices. In that regard, it is particularly understood that the different processing and/or control aspects of the present disclosure may be implemented separately or within pre-defined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the processing system 101 being located in the control room. In other embodiments, the processing system 101 may be located elsewhere, such as in the catheter lab 102, in a centralized area in the medical facility, or at an off-site location. The catheter lab 102 includes a sterile field but its associated control room 104 may or may not be sterile depending on the requirements of a procedure and/or health care facility. The catheter lab and control room may be used to perform on a patient any number of medical procedures such as angiography, intravascular ultrasound (IVUS), virtual histology (VH), forward looking IVUS (FL-IVUS), intravascular photoacoustic (IVPA) imaging, near-infrared Spectroscopy (NIRS), a fractional flow reserve (FFR) determination or other pressure-based determination (e.g., iFR), a coronary flow reserve (CFR) determination, optical coherence tomography (OCT), intravascular OCT, computed tomography (CT), intracardiac echocardiography (ICE), forward-looking ICE (FLICE), intravascular palpography, transesophageal ultrasound, or any other medical sensing modalities known in the art. Further, the catheter lab and control room may be used to perform one or more treatment or therapy procedures on a patient such as radiofrequency ablation (RFA), cryotherapy, atherectomy, stenting, or any other medical treatment procedure known in the art. For example, in catheter lab 102 a patient 106 may be undergoing a multi-modality procedure either as a single procedure or in combination with one or more sensing procedures. In any case, the catheter lab 102 includes a plurality of medical instruments including medical sensing devices that may collect medical sensing data in various different medical sensing modalities from the patient 106.

Instruments 108 and 110 are medical sensing devices that may be utilized by a clinician to acquire medical sensing data about the patient 106. In a particular instance, the device 108 collects medical sensing data in one modality and the device 110 collects medical sensing data in a different modality. For instance, the instruments may each collect one of pressure, flow (velocity), images (including images obtained using ultrasound (e.g., IVUS), OCT, IVPA, intravascular MRI, thermal, ICE, Trans Esophageal Echo (TEE), Trans Thoracic Echo (TTE) and/or other internal imaging techniques), temperature, and/or combinations thereof. The instruments 108 and 110 may be any form of device, instrument, or probe sized and shaped to be positioned within a vessel, attached to an exterior of the patient, or scanned across a patient at a distance.

In the illustrated embodiment of FIG. 1, instrument 108 is an intravascular IVUS catheter that may include one or more sensors such as a phased-array transducer to collect IVUS sensing data. In some embodiments, the IVUS catheter may be capable of multi-modality sensing such as IVUS and IVPA sensing. Further, in the illustrated embodiment, the instrument 110 is an intravascular OCT catheter that may include one or more optical sensors configured to collect OCT sensing data. In a further embodiment, a single instrument incorporates aspects of the functionalities (e.g., data acquisition) of both instruments 108 and 110. In the illustrated embodiment of FIG. 1, an IVUS patient interface module (PIM) 112 and an OCT PIM 114 respectively couple the instrument 108 and instrument 110 to the medical system 100. In particular, the IVUS PIM 112 and the OCT PIM 114 are operable to respectively receive medical sensing data collected from the patient 106 by the instrument 108 and instrument 110 and are operable to transmit the received data to the processing system 101 in the control room 104. In one embodiment, the PIMs 112 and 114 include analog to digital (A/D) converters and transmit digital data to the processing system 101, however, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In other instances, the PIMs may be connected to the processing system 101 via wireless connections using IEEE 802.11 Wi-Fi standards, Ultra Wide-Band (UWB) standards, wireless FireWire, wireless USB, or another high-speed wireless networking standard. In further embodiments, the connection hardware and functionality of the PIMs 112 and 114 is implemented in a single PIM that is coupled to both of instruments 108 and 110.

Additionally, in the medical system 100, an electrocardiogram (ECG) device 116 is operable to transmit electrocardiogram signals or other hemodynamic data from patient 106 to the processing system 101. In some embodiments, the processing system 101 may be operable to synchronize data collected with the instruments 108 and 110 using ECG signals from the ECG 116. Further, an external imaging system 117 is operable to collect x-ray images, angiogram images, ultrasound images, two or three-dimensional computed tomography (CT) images, computed tomography angiogram (CTA) images, positron emission tomography (PET) images, PET-CT images, magnetic resonance images (MRI), single-photon emission computed tomography (SPECT) images, and/or any combination of the above images of the patient 106 and transmit them to the processing system 101. In one embodiment, the external imaging system 117 may be communicatively coupled to the processing system to the processing system 101 through an adapter device. Such an adaptor device may transform data from a proprietary third-party format into a format usable by the processing system 101. As will be explained in greater detail below, in some embodiments, the processing system 101 may be operable to co-register image data from external imaging system 117 (e.g., x-ray data, MRI data, CT data, etc.) with sensing data from the instruments 108 and 110 and other instruments internal and external to the catheter lab. As one aspect of this, the co-registration may be performed to generate three-dimensional images with the sensing data. In another embodiment, medical data from the ECG and/or external imaging system 117 may be temporally co-registered with medical data captured by either of (or both) instruments 108 and 110. Spatial and temporal co-registration will be discussed in greater detail in association with FIGS. 5-11.

A bedside controller 118 is also communicatively coupled to the processing system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). The bedside controller 118 is capable displaying workflows and diagnostic images for multiple modalities allowing a clinician to control the acquisition of multi-modality medical sensing data with a single interface device.

A main controller 120 in the control room 104 is also communicatively coupled to the processing system 101 and, as shown in FIG. 1, is adjacent to catheter lab 102. In the current embodiment, the main controller 120 is similar to the bedside controller 118 in that it includes a touch screen and is operable to display a multitude of GUI-based workflows corresponding to different medical sensing modalities via a UI framework service executing thereon. In some embodiments, the main controller 120 may be used to simultaneously carry out a different aspect of a procedure's workflow than the bedside controller 118. In alternative embodiments, the main controller 120 may include a non-interactive display and standalone controls such as a mouse and keyboard.

The medical system 100 further includes a boom display 122 communicatively coupled to the processing system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, in some embodiments, the multi-modality processing system 101 is communicatively coupled to a data network such as a TCP/IP-based local area network (LAN), a Synchronous Optical Networking (SONET) network, or a wide area network (WAN) or the Internet. The processing system 101 may connect to various resources via such a network. For example, the processing system 101 may communicate with a Digital Imaging and Communications in Medicine (DICOM) system, a Picture Archiving and Communication System (PACS), and a Hospital Information System (HIS) through the network.

Additionally, in the illustrated embodiment, medical instruments in system 100 discussed above are shown as communicatively coupled to the processing system 101 via a wired connection such as a standard copper link or a fiber optic link, but, in alternative embodiments, the tools may be connected to the processing system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the processing system 101 so as to contribute additional and/or different functionality to the medical system 100.

Figure 2:
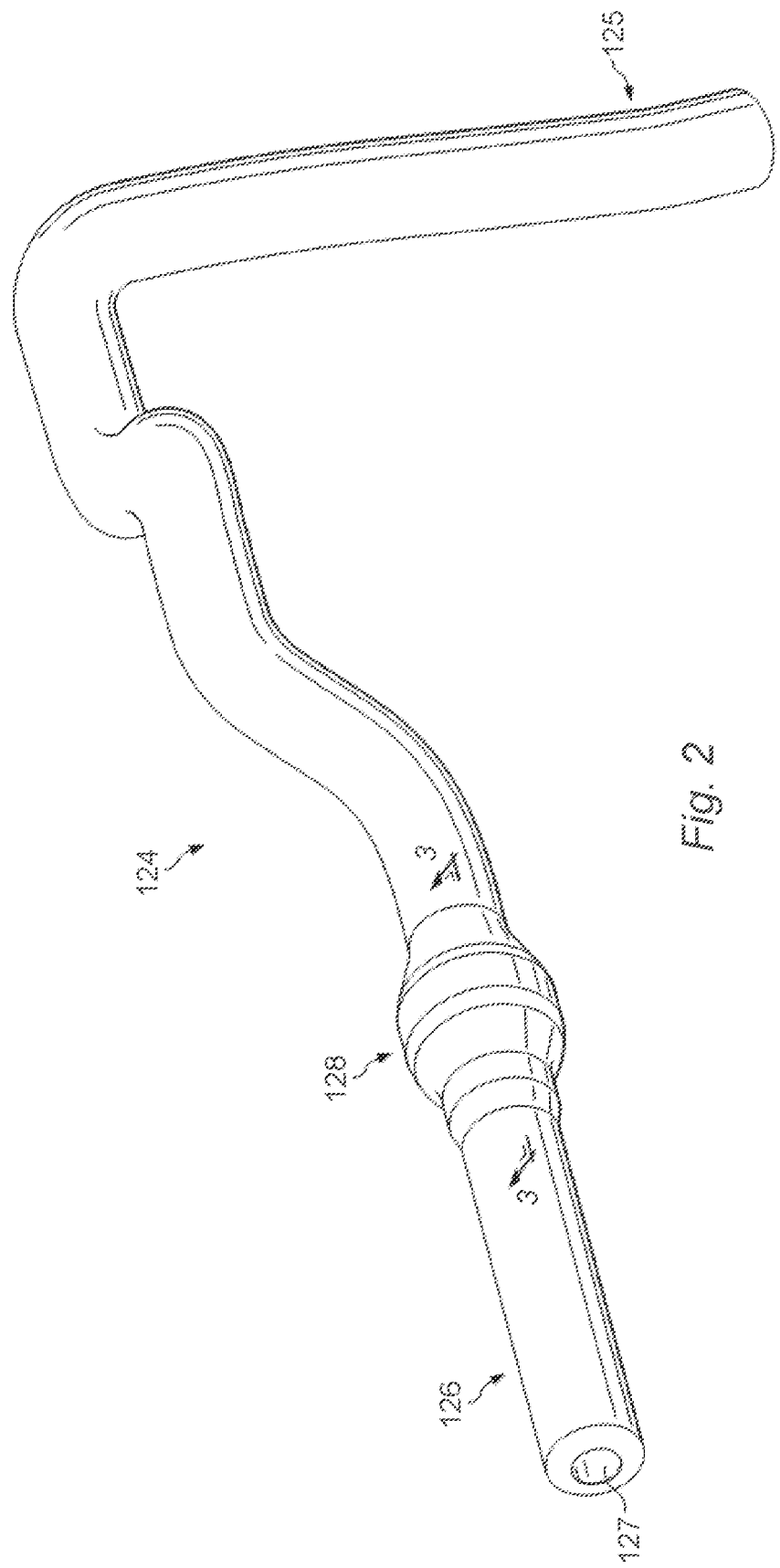
FIG. 2 is a diagrammatic perspective view of a vessel having a stenosis according to an embodiment of the present disclosure.

Referring to FIG. 2, shown therein is a vessel 124 having a stenosis according to an embodiment of the present disclosure. In that regard, FIG. 2 is a diagrammatic perspective view of the vessel 124 that includes a proximal portion 125 and a distal portion 126. A lumen 127 extends along the length of the vessel 124 between the proximal portion 125 and the distal portion 126. In that regard, the lumen 127 is configured to allow the flow of fluid through the vessel. In some instances, the vessel 124 is a systemic blood vessel. In some particular instances, the vessel 124 is a coronary artery. In such instances, the lumen 127 is configured to facilitate the flow of blood through the vessel 124.

As shown, the vessel 124 includes a stenosis 128 between the proximal portion 125 and the distal portion 126. Stenosis 128 is generally representative of any blockage or other structural arrangement that results in a restriction to the flow of fluid through the lumen 127 of the vessel 124. Embodiments of the present disclosure are suitable for use in a wide variety of vascular applications, including without limitation coronary, peripheral (including but not limited to lower limb, carotid, and neurovascular), renal, and/or venous. Where the vessel 124 is a blood vessel, the stenosis 128 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Note that the stenosis 128 is exemplary in nature and should not be considered limiting in any way. In that regard, it is understood that the stenosis 128 has other shapes and/or compositions that limit the flow of fluid through the lumen 127 in other instances. While the vessel 124 is illustrated in FIG. 2 as having a single stenosis 128 and the description of the embodiments below is primarily made in the context of a single stenosis, it is nevertheless understood that the devices, systems, and methods described herein have similar application for a vessel having multiple stenosis regions.

Figure 3:
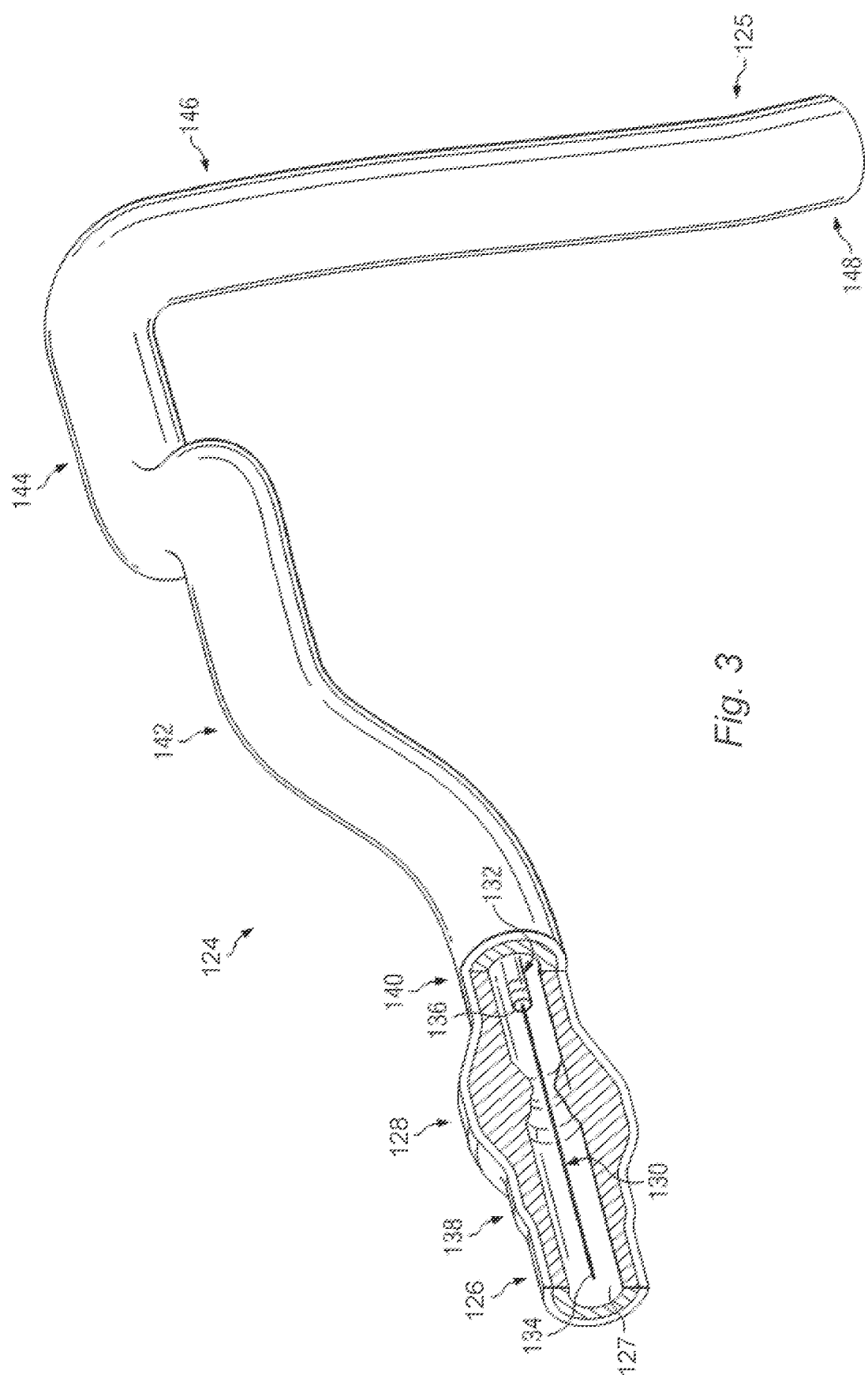
FIG. 3 is a diagrammatic, partial cross-sectional perspective view of a portion of the vessel of FIG. 2 taken along section line 3-3 of FIG. 2.

Referring now to FIG. 3, illustrated is a partial cross-sectional perspective view of a portion of the vessel 124 taken along section line 3-3 of FIG. 2. In particular, the vessel 124 is shown with instruments 130 and 132 positioned therein according to an embodiment of the present disclosure. In general, instruments 130 and 132 may be any form of device, instrument, or probe sized and shaped to be positioned within a vessel. In that regard, in some instances instrument 132 is suitable for use as at least one of instruments 108 and 110 discussed above. Accordingly, in some instances the instrument 132 includes features similar to those discussed above with respect to instruments 108 and 110. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In that regard, the single instrument incorporates aspects of the functionalities (e.g., data acquisition) of both instruments 130 and 132 in some embodiments.

Instrument 130 is configured to obtain medical diagnostic information (data) about the vessel 124. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS, IVPA, etc.), intravascular OCT, near-infrared Spectroscopy (NIRS), intravascular MRI, thermal, and/or other endoluminal imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 may include at least one element configured to monitor pressure within the vessel 124. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 128 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 124. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The medical diagnostic information (data) obtained by instrument 132 includes one or more of pressure, flow (velocity), images (including images obtained using ultrasound (e.g., IVUS, IVPA, etc.), intravascular OCT, NIRS, intravascular MRI, thermal, and/or other endoluminal imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 may also include at least one element configured to monitor pressure within the vessel 124. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Millar catheters are utilized in some embodiments. Currently available catheter products suitable for use with one or more of Philips's Xper Flex Cardio Physiomonitoring System, GE's Mac-Lab XT and XTi hemodynamic recording systems, Siemens's AXIOM Sensis XP VC11, McKesson's Horizon Cardiology Hemo, and Mennen's Horizon XVu Hemodynamic Monitoring System and include pressure monitoring elements can be utilized for instrument 132 in some instances.

In accordance with some aspects of the present disclosure, at least one of the instruments 130 and 132 may be configured to monitor a pressure within the vessel 124 distal of the stenosis 128 and at least one of the instruments 130 and 132 may be configured to monitor a pressure within the vessel proximal of the stenosis. In that regard, the instruments 130, 132 are sized and shaped to allow positioning of the at least one element configured to monitor pressure within the vessel 124 to be positioned proximal and/or distal of the stenosis 128 as necessary based on the configuration of the devices. In that regard, FIG. 3 illustrates a position 138 suitable for measuring pressure distal of the stenosis 128. In that regard, the position 138 is less than 5 cm, less than 3 cm, less than 2 cm, less than 1 cm, less than 5 mm, and/or less than 2.5 mm from the distal end of the stenosis 128 (as shown in FIG. 2) in some instances. FIG. 3 also illustrates a plurality of suitable positions for measuring pressure proximal of the stenosis 128. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 128 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In one embodiment, the instrument 132 includes both a pressure sensor and an imaging sensor, such as an IVUS, IVPA, OCT, NIRS, or MRI senor. In such an embodiment, the plurality of sensors disposed on the instruments 130 and 132 may be utilized to perform a multi-modality diagnostic and/or treatment procedure. For example, the pressure sensor disposed on instrument 130 and the pressure sensor disposed on instrument 132 may collect medical data for an FFR calculation, and the imaging sensor disposed on instrument 132 may collect medical data to be processed into diagnostic images to be displayed to a practitioner and/or analyzed in an automated manner by the processing system 101. As will be discussed below in greater detail, pressure data and diagnostic image data collected over a time period may be co-registered in various manners to enable physiological evaluation of a patient's vessel over the time period. In one embodiment, pressure data and diagnostic image data are collected both before and after a medical procedure (such as a stent placement or a non-invasive drug treatment) and co-registered temporally and spatially to facilitate accurate evaluation of a patient's physiological response to the procedure. Such temporal and spatial co-registration techniques may utilize any type of collected medical data discussed herein, including OCT data, angiogram data, MIII data, intravascular MIII data, FFR data, IVUS data, VH data, FL-IVUS data, IVPA data, CFR data, CT data, PET data, SPECT data, ICE data, FLICE data, intravascular palpography data, transesophageal ultrasound data, or any other medical data known in the art.

Additionally, the instruments 130 and 132 may be sized and shaped to allow concurrent positioning of additional catheter-type instruments within the vessel 124. For instance, in one embodiment, the instrument 108 may have a greater diameter than the instrument 132, permitting it to slide over both instruments 130 and 132 and into a position near the stenosis 128. Once positioned, the instrument 108 may collect medical data associated with the vessel 124 using an IVUS sensor. During a multi-modality procedure, the collection of IVUS data may occur concurrently or subsequently to any collection of data with instruments 130 and 132. It is understood that the instruments 130 and 132 may be sized and shaped to allow any number of additional instruments to be positioned within the vessel 124 during a multi-modality procedure.

Figure 4:
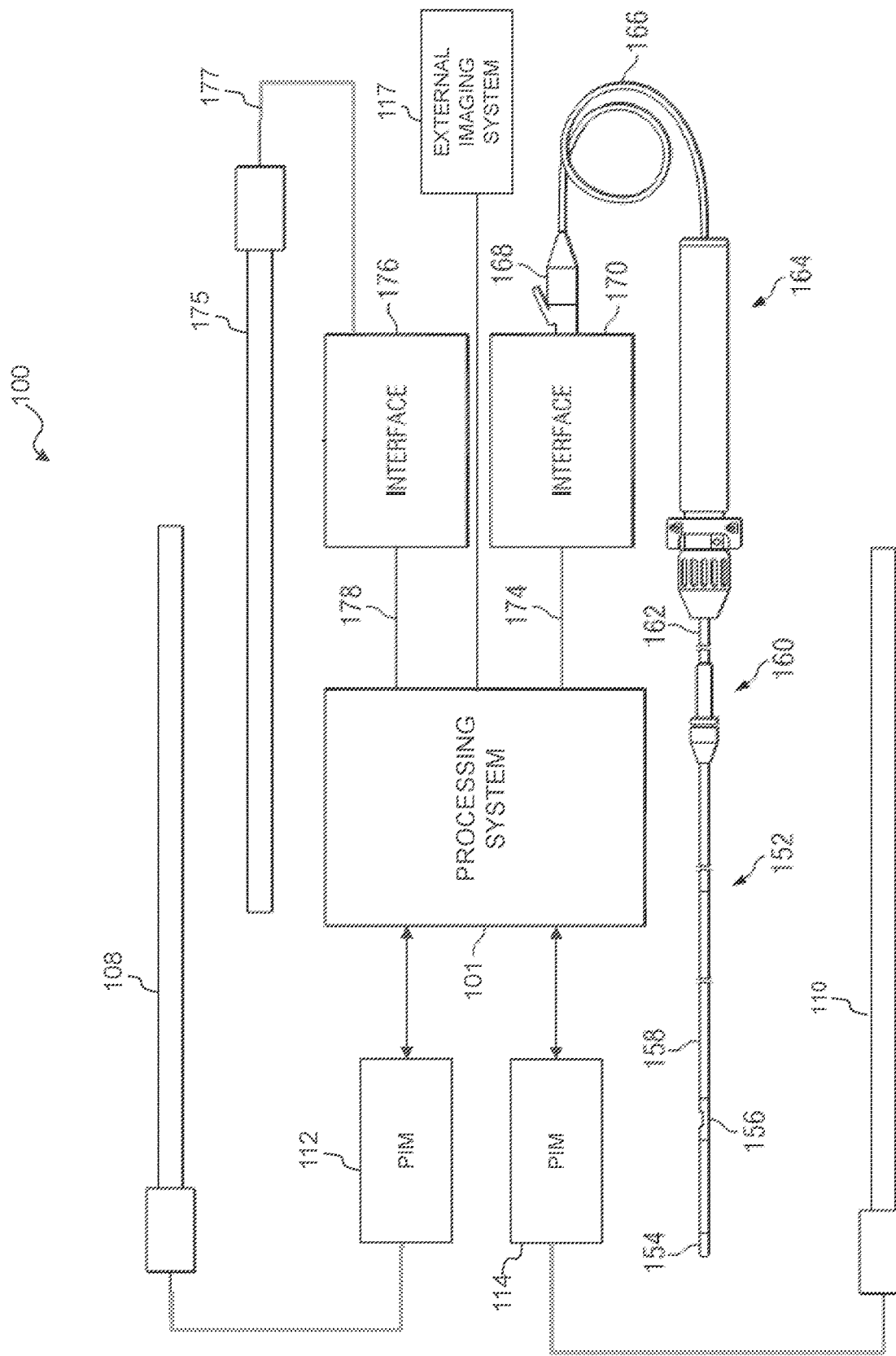
FIG. 4 is a diagrammatic, schematic view of a medical system according to an embodiment of the present disclosure.

Referring now to FIG. 4, illustrated is a diagrammatic, schematic view of portions of the medical system 100 according to aspects of the present disclosure. As shown, in addition to the intravascular instruments 108 and 110, the medical system 100 includes the external imaging system 117, as discussed above. The external imaging system may generate diagnostic images such as x-ray images, angiogram images, CT images, PET images, PET-CT images, MIII images, SPECT images, and/or other extraluminal diagnostic images, and such images may be co-registered with the internal-based diagnostic data and images generated by the intravascular instruments 108 and 110. The medical system 100 includes also an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. The housing 156 may contain a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof. The interface 170 is communicatively coupled to the multi-modality processing system 101 via a connection 174.

Together, connector 164, cable 166, connector 168, interface 170, and connection 174 facilitate communication between the one or more sensors, transducers, and/or other monitoring elements of the instrument 152 and the processing system 101. However, this communication pathway is exemplary in nature and should not be considered limiting in any way. In that regard, it is understood that any communication pathway between the instrument 152 and the processing system 101 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the processing system 101 is positioned remote from an operating area where the instrument 152 is being used in some instances. Having the connection 174 include a connection over a network can facilitate communication between the instrument 152 and the remote processing system 101 regardless of whether the processing system is in an adjacent room, an adjacent building, or in a different state/country. Further, it is understood that the communication pathway between the instrument 152 and the processing system 101 is a secure connection in some instances. Further still, it is understood that, in some instances, the data communicated over one or more portions of the communication pathway between the instrument 152 and the processing system 101 is encrypted.

The medical system 100 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. Instrument 175 may include a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the processing system 101 via a connection 178.

Similar to the connections between instrument 152 and the processing system 101, interface 176 and connections 177 and 178 facilitate communication between the one or more sensors, transducers, and/or other monitoring elements of the instrument 175 and the processing system 101.

However, this communication pathway is exemplary in nature and should not be considered limiting in any way. In that regard, it is understood that any communication pathway between the instrument 175 and the processing system 101 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the processing system 101 is positioned remote from an operating area where the instrument 175 is being used in some instances. Having the connection 178 include a connection over a network can facilitate communication between the instrument 175 and the remote processing system 101 regardless of whether the processing system is in an adjacent room, an adjacent building, or in a different state/country. Further, it is understood that the communication pathway between the instrument 175 and the processing system 101 is a secure connection in some instances. Further still, it is understood that, in some instances, the data communicated over one or more portions of the communication pathway between the instrument 175 and the processing system 101 is encrypted.

It is understood that one or more components of the medical system 100 are not included, are implemented in a different arrangement/order, and/or are replaced with an alternative device/mechanism in other embodiments of the present disclosure. For example, in some instances, the medical system 100 does not include interface 170 and/or interface 176. In such instances, the connector 168 (or other similar connector in communication with instrument 152 or instrument 175) may plug into a port associated with processing system 101. Alternatively, the instruments 108, 110, 152, and 175 may communicate wirelessly with the processing system 101. Generally speaking, the communication pathway between either or both of the instruments 108, 110, 152, and 175 and the processing system 101 may have no intermediate nodes (i.e., a direct connection), one intermediate node between the instrument and the processing system, or a plurality of intermediate nodes between the instrument and the processing system.

Additionally, the instruments 108, 110, 152, and 175 may be sized and shaped to allow concurrent positioning of additional catheter-type instruments within a vessel. For instance, in one embodiment, the instrument 108 may have a greater diameter than the instrument 175, permitting it to slide over both instruments 152 and 175 and into a position near a position of interest within a vessel. In turn, the instrument 110 may have a diameter greater than the instrument 108, permitting it to slide over instruments 108, 152 and 175. Once positioned, the instruments 108 and 110 may collect medical data using IVUS, IVPA, OCT, intravascular MRI, and/or another type of imaging sensors concurrently or subsequently to any collection of data with instruments 130 and 132. During such a multi-modality procedure, spatial co-registration of different types of data may be carried out in various manners. And, during a subsequent single or multi-modality procedure, spatial co-registration may be performed with the data collected in the previous procedure and the data collected in the subsequent procedure. In that regard, the figures below illustrate various manners in which to temporally and spatially co-register single and multi-modality diagnostic data.

Diagnostic information within a vasculature of interest can be obtained using one or more of instruments 108, 110, 130, 132, 152, and 175, as well as external imaging system 117. For example, diagnostic information is obtained for one or more coronaries arteries, peripheral arteries, cerebrovascular vessels, etc. The diagnostic information can include pressure-related values, flow-related values, diagnostic images of intravascular portions of the patient, etc. Pressure-related values can include FFR, Pd/Pa (e.g., a ratio of the pressure distal to a lesion to the pressure proximal to the lesion), iFR (e.g., a pressure ratio value calculated using a diagnostic window relative to a distance as a first instrument is moved through a vessel relative to a second instrument, including across at least one stenosis of the vessel), etc. Flow-related values can include coronary flow reserve or CFR (e.g., maximum increase in blood flow through the coronary arteries above the normal resting volume), basal stenosis resistance index (BSR), etc.

In some embodiments, the diagnostic information obtained by the external imaging system 117 can include externally-obtained angiographic images, x-ray images, CT images, PET images, MRI images, SPECT images, and/or other two-dimensional or three-dimensional extraluminal depictions of a patient's vasculature. The diagnostic information and/or data obtained by instruments 108, 110, 130, 132, 152, and/or 175 are correlated or co-registered to angiographic image(s) and/or other two-dimensional or three-dimensional depictions of a patient's vasculature obtained by the external imaging system 117. Spatial co-registration can be completed using techniques disclosed in U.S. Pat. No. 7,930,014, titled "VASCULAR IMAGE CO-REGISTRATION," which is hereby incorporated by reference in its entirety, based on the known pullback speed/distance, based on a known starting point, based on a known ending point, and/or combinations thereof. In some embodiments, diagnostic information and/or data is correlated to vessel images using techniques similar to those described in U.S. patent application Ser. No. 14/144,280 published as U.S. Patent Application Publication No. 2014/0187920 on Jul. 3, 2014, which is hereby incorporated by reference in its entirety. In some embodiments, co-registration and/or correlation can be completed as described in U.S. patent application Ser. No. 14/335,603 published as U.S. Patent Application Publication No. 2015/0025330 on Jan. 22, 2015, which is hereby incorporated by reference in its entirety. In other embodiments, co-registration and/or correlation can be completed as described in International Application No. PCT/IL2011/000612 published as WO2012/014212 on Feb. 2, 2012, which is hereby incorporated by reference in its entirety. Further, in some embodiments, co-registration and/or correlation can be completed as described in International Application No. PCT/IL2009/001089 published as WO2010/058398 on May 27, 2010, which is hereby incorporated by reference in its entirety. Additionally, in other embodiments, co-registration and/or correlation can be completed as described in U.S. patent application Ser. No. 12/075,244 published as U.S. Patent Application Publication No. 2008/0221442 on Sep. 11, 2008, which is hereby incorporated by reference in its entirety.

Referring now to FIGS. 5-8, illustrated are a stylized images of a portion of a patient's vasculature according to embodiments of the present disclosure. One of ordinary skill in the art would recognize that the images of FIGS. 5-8 are simply examples, and the intravascular elements depicted in FIGS. 5-8 may correspond to any blood vessel—coronary, systemic, pulmonary, or otherwise—in a patient. Further, FIGS. 5-8 may be displayed on a display of a system assessing a patient's vasculature, such as display 118 and/or display 122 associated with the processing system 101 (FIGS. 1, 4). That is, one or more components (e.g., a processor, processing circuit, and/or dedicated graphics processor, etc.) of the system 101 may cause the display of the images shown in FIGS. 5-8.

Figure 5:
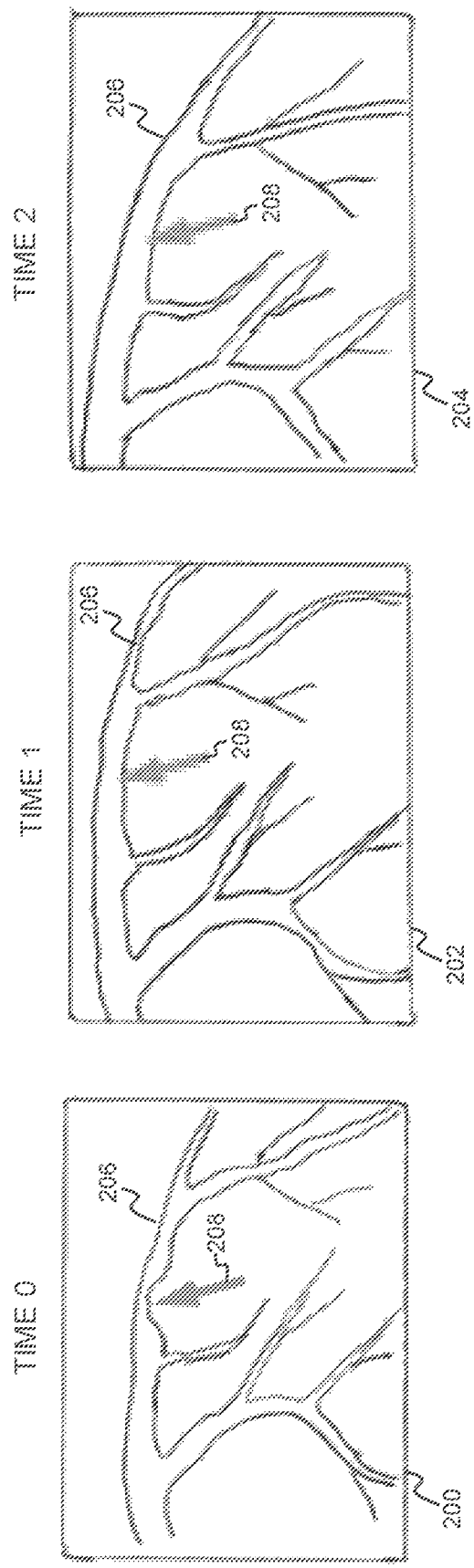

In more detail, FIG. 5 illustrates three extraluminal images 200, 202, and 204 of a vessel 206 at three different times: time 0, time 1, and time 2. The extraluminal images 200, 202, and 204 may be generated by the external imaging system 117 (FIGS. 1, 4) and may be angiographic images, x-ray images, CT images, PET images, MRI images, SPECT images, and/or other two-dimensional or three-dimensional depictions of the patient's vasculature. The extraluminal images 200, 202, and 204 may all be associated with the same extraluminal imaging modality or they may be associated with different extraluminal imaging modalities. The points in time represented by time 0, time 1, and time 2 may be any three successive points in time. For instance, they may be three points during the course of a longitudinal study that a practitioner deems useful in evaluating the physiological condition of the patient's vasculature. In one embodiment, the longitudinal study may assess the effectiveness of a medical procedure performed before or during the study. The medical procedure may be an invasive procedure such as the insertion of an intravascular stent or it may be a non-invasive procedure such as the administration of a drug. Additionally, the extraluminal images 200, 202, and 204 include an arrow 208 that points to an area of interest in the vessel 206. In the illustrated embodiment, the area of interest includes a stenosis that is generally representative of any blockage or other structural arrangement that results in a restriction to the flow of fluid through the vessel 206.

As mentioned above, the extraluminal image 200 was captured at time 0, which, in the illustrated embodiment, represents a point in time before an intravascular procedure was performed on the vessel 206 to treat the stenosis. The extraluminal image 202 was captured at time 1, which represents a point in time subsequent to the intravascular procedure being performed on the vessel 206. Minutes, hours, days, weeks, months, or years may have passed between time 0 and time 1. In the illustrated embodiment, the vessel 206 shows fewer signs of blockage in the area of interest at time 1. In one embodiment, the extraluminal image 202 was captured immediately after the insertion of a stent during the course of the intravascular procedure. In another embodiment, the extraluminal image 202 was captured during a follow-up visit subsequent to the intravascular procedure. The extraluminal image 204 was captured at time 2, which represents a point in time subsequent to time 1. Minutes, hours, days, weeks, months, or years may have passed between time 1 and time 2. In one embodiment, the extraluminal image 204 was captured during a first or subsequent follow-up visit after the intravascular procedure. Although, FIG. 5 depicts three extraluminal images captured at three points in time, a greater or fewer number of extraluminal images may be captured at greater or fewer number of points in time.

In one embodiment, the extraluminal images 200, 202, and 204 are displayed concurrently on a display associated with the processing system 101 so that a practitioner may evaluate any changes in the physiological condition of the vessel 206 over time. Spatial co-registration may be performed on the extraluminal images 200, 202, and 204 so that the same portions of the patient's vasculature are displayed in each of the extraluminal images. Such spatial co-registration positionally aligns the extraluminal images 200, 202, and 204 whether they are all associated with the same imaging modality (e.g., CT) or whether they are associated with two or more different imaging modalities (e.g., CT and PET). In some embodiments, spatial co-registration may be performed so as to place the area of interest in the vessel 206—as pointed to by the arrow 208—at the same relative position in each of the extraluminal images 200, 202, and 204. Placing the area of interest in the same position—such as the center—in each of the extraluminal images 200, 202, and 204 may allow a practitioner to evaluate changes in the physiological condition of the vessel 206 in a more efficient manner. Such co-registration may be accomplished using one or more of the co-registration techniques incorporated by reference above.

Figure 6:
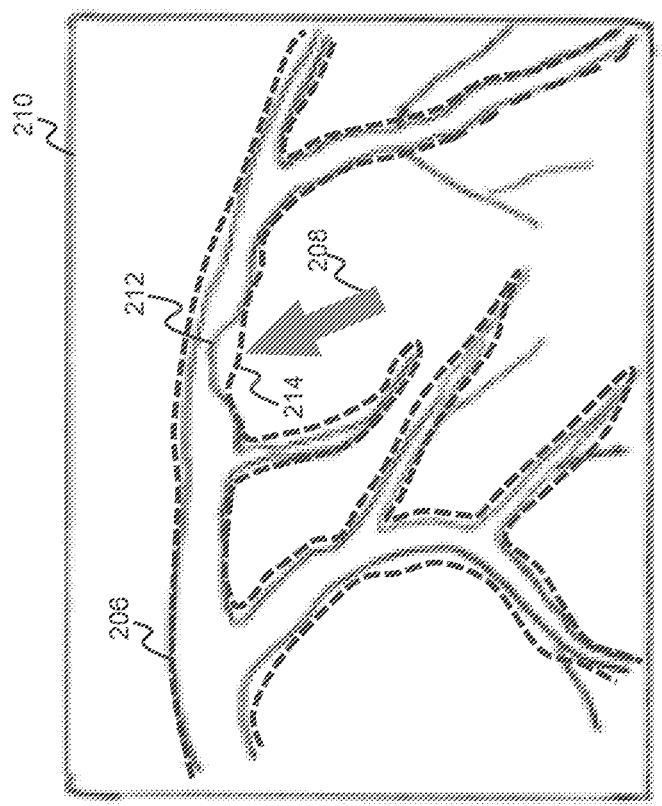

Referring now to FIG. 6, illustrated is a composite extraluminal image 210 according to an embodiment of the present invention. Specifically, the extraluminal image 210 depicts a combination of the extraluminal image 200 and the extraluminal image 202 from FIG. 5. A solid line 212 represents the outline of the vessel 206 as depicted in the extraluminal image 200 captured at time 0, and the broken line 214 represents the outline of the vessel 206 as depicted in the extraluminal image 202 captured at time 1. In the illustrated embodiment, the extraluminal images 200 and 202 have been spatially aligned using co-registration techniques, such as those co-registration techniques discussed above and/or those incorporated by reference. In some embodiments, the processing system 101 may automatically (i.e., without human intervention) co-register two or more images using one or more co-registration algorithms implemented in software and/or hardware. After co-registration, the composite extraluminal image 210 may be generated by the processing system 101 and visually output on a display so that a practitioner may evaluate any changes in the physiological condition of the vessel 206 over time.

As shown in the composite extraluminal image 210, the solid line 212 of the extraluminal image 200 and the broken line 214 of the extraluminal image 202 are substantially aligned for a majority of patient's vasculature depicted in the extraluminal image 210. However, at the area of interest in the vessel 206 pointed to by the arrow 208, the lines 210 and 212 diverge, indicating that some physiological change has happened to the vessel between time 0 and time 1. In the illustrated example, the performance of an intravascular procedure between time 0 and time 1 has lessened the severity of a stenosis. That is, the vessel lumen is wider at time 1 than at time 0, as shown by the composite extraluminal image 210. In this manner, by spatially co-registering the extraluminal image 200 and the extraluminal image 202 and displaying a composite on a display device, a practitioner can quickly visually identify the changes in a patient's physiological condition and determine if the intravascular procedure was successful.

In additional embodiments, more than two images of a patient's vasculature may be co-registered and combined into a composite image for display to a practitioner. In that regard, two or three or four or more images may be registered to a common time point, such as time 0. Additionally, in some embodiments, the processing system 101 may automatically determine any change in the physiological condition of the vessel 206 based on an automated analysis of the composite extraluminal image 210. In that regard, after such analysis, the processing system 101 may output a textual and/or graphical report highlighting any changes in the physiological condition of the vessel for consideration by a practitioner. The processing system 101 may include software and/or hardware modules configured to perform such analysis.

Figure 8:
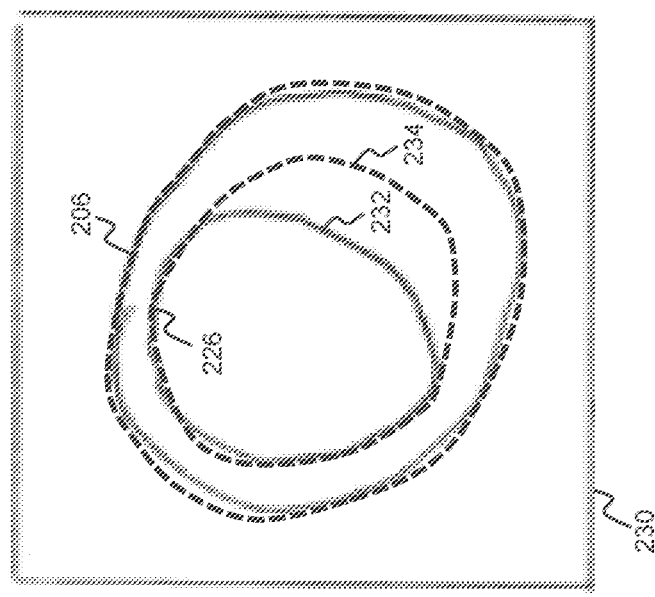

Referring now to FIGS. 7 and 8, illustrated are three endoluminal images 220, 222, and 224 of the vessel 206 at three different times: time 0, time 1, and time 2. The endoluminal images 220, 222, and 224 may be generated by using one or more of the catheter-based instruments 108, 110, 130, 132, 152, and 175 (FIGS. 1, 4) and may be IVUS images, FL-IVUS images, IVPA images, OCT images, NIRS images, or intravascular MRI images, and/or other two-dimensional or three-dimensional depictions of the patient's vasculature captured from within the patient's vasculature. The endoluminal images 220, 222, and 224 may all be associated with the same endoluminal imaging modality or they may be associated with different endoluminal imaging modalities. The points in time represented by time 0, time 1, and time 2 may be any three successive points in time, such as the points in time described in association with FIGS. 5 and 6 that are deemed significant in a longitudinal study. In the illustrated embodiment, endoluminal images 220, 222, and 224 depict an area of interest of the vessel 206 that includes a stenosis generally representative of any blockage or other structural arrangement that results in a restriction to the flow of fluid through the vessel. The area of interest shown in FIG. 6 may be the same area of interest as pointed to by the arrow 208 in FIG. 5. As shown in the endoluminal images 220, 222, and 224, the vessel 206 includes a lumen 226 configured to allow the flow of fluid through the vessel.

The endoluminal image 220 was captured at time 0, which, in the illustrated embodiment, represents a point in time before an intravascular procedure was performed on the vessel 206 to remove the stenosis. The endoluminal image 222 was captured at time 1, which represents a point in time subsequent to the intravascular procedure being performed on the vessel 206. In the illustrated example, a stent 228 has been placed in the lumen 226 as part of the intravascular procedure. Minutes, hours, days, weeks, months, or years may have passed between time 0 and time 1. At time 1, as compared to time 0, the lumen 228 has a larger diameter, indicating that the intravascular procedure was generally successful. In one embodiment, the endoluminal image 222 was captured immediately after the insertion of the stent 228 during the course of the intravascular procedure. In another embodiment, the endoluminal image 222 was captured during a follow-up visit after the intravascular procedure. The endoluminal image 224 was captured at time 2, which represents a point in time subsequent to time 1. Minutes, hours, days, weeks, months, or years may have passed between time 1 and time 2. In one embodiment, the endoluminal image 224 was captured during a first or subsequent follow-up visit after the intravascular procedure. Although FIG. 7 depicts three endoluminal images captured at three points in time, a greater or fewer number of endoluminal images may be captured at greater or fewer number of points in time.

Additionally, although FIG. 7 depicts several points in time during a longitudinal study meant to assess the effectiveness of a stent, the longitudinal study may alternatively assess the effectiveness of a non-invasive procedure. For example, a drug to reduce the stenosis may have been administered sometime before or during the time span represented by times 0, 1, and 2, and the endoluminal images may allow a practitioner to evaluate whether the stenosis was affected by the administration of the drug.

In one embodiment, the endoluminal images 220, 222, and 224 may be displayed concurrently on a display associated with the processing system 101 so that a practitioner may evaluate any changes in the physiological condition of the vessel 206 over time. Spatial co-registration may be performed on the endoluminal images 220, 222, and 224 so that the same portions of the patient's vasculature are displayed in each of the endoluminal images. Such spatial co-registration positionally aligns the endoluminal images 220, 222, and 224 whether they are all associated with the same imaging modality (e.g., IVUS) or whether they are associated with two or more different imaging modalities (e.g., IVUS and OCT). In some embodiments, spatial co-registration may be performed so as to place a specific portion of the vessel 206 at the same relative position in each of the endoluminal images 220, 222, and 224. Placing the same portion of the vessel—such as the center—in the same position in each of the endoluminal images 220, 222, and 224 may allow a practitioner to compare the condition of the vessel at the area of interest in a more efficient manner.

Referring now to FIG. 8, illustrated is a composite endoluminal image 230 according to an embodiment of the present invention. Specifically, the endoluminal image 230 depicts a combination of the endoluminal image 220 and the endoluminal image 222 from FIG. 7. A solid line 232 represents the outline of the vessel 206 and lumen 226 as depicted in the endoluminal image 220 captured at time 0, and the broken line 234 represents the outline of the vessel 206 and lumen 226 as depicted in the endoluminal image 222 captured at time 1. In the illustrated embodiment, the endoluminal images 220 and 222 have been spatially aligned using one or more of the co-registration techniques incorporated by reference above. In some embodiments, the processing system 101 may automatically (i.e., without human intervention) spatially align two or more images using one or more co-registration algorithms implemented in software and/or hardware. After co-registration, the composite endoluminal image 230 may be generated by the processing system 101 and visually output on a display so that a practitioner may evaluate any changes in the physiological condition of the vessel 206 over time.

As shown in the composite endoluminal image 230, the solid line 232 of the endoluminal image 220 and the broken line 234 of the endoluminal image 222 are substantially aligned with the regard to the outer circumference of the vessel 206. However, with regard to the lumen 226, the lines 232 and 234 diverge, indicating that some physiological change has happened to the vessel between time 0 and time 1. In the illustrated example, the performance of an intravascular procedure between time 0 and time 1 has increased the diameter of the lumen 226, and thus, lessened the severity of a stenosis. In this manner, by spatially co-registering the endoluminal image 220 and the endoluminal image 222 and displaying a composite on a display device, a practitioner can quickly visually access the change in a patient's physiological condition and determine if the intravascular procedure was successful.

In additional embodiments, more than two endoluminal images of a patient's vasculature may be co-registered and combined into a composite image for display to a practitioner. Additionally, in some embodiments, the processing system 101 may automatically determine any change in the physiological condition of the vessel 206 and lumen 226 based on an automated analysis of the composite endoluminal image 230. In that regard, after such analysis the processing system 101 may output a textual and/or graphical report highlighting any changes in the physiological condition of the vessel for consideration by a practitioner. The processing system 101 may include software and/or hardware modules configured to perform such analysis.

Figure 9:
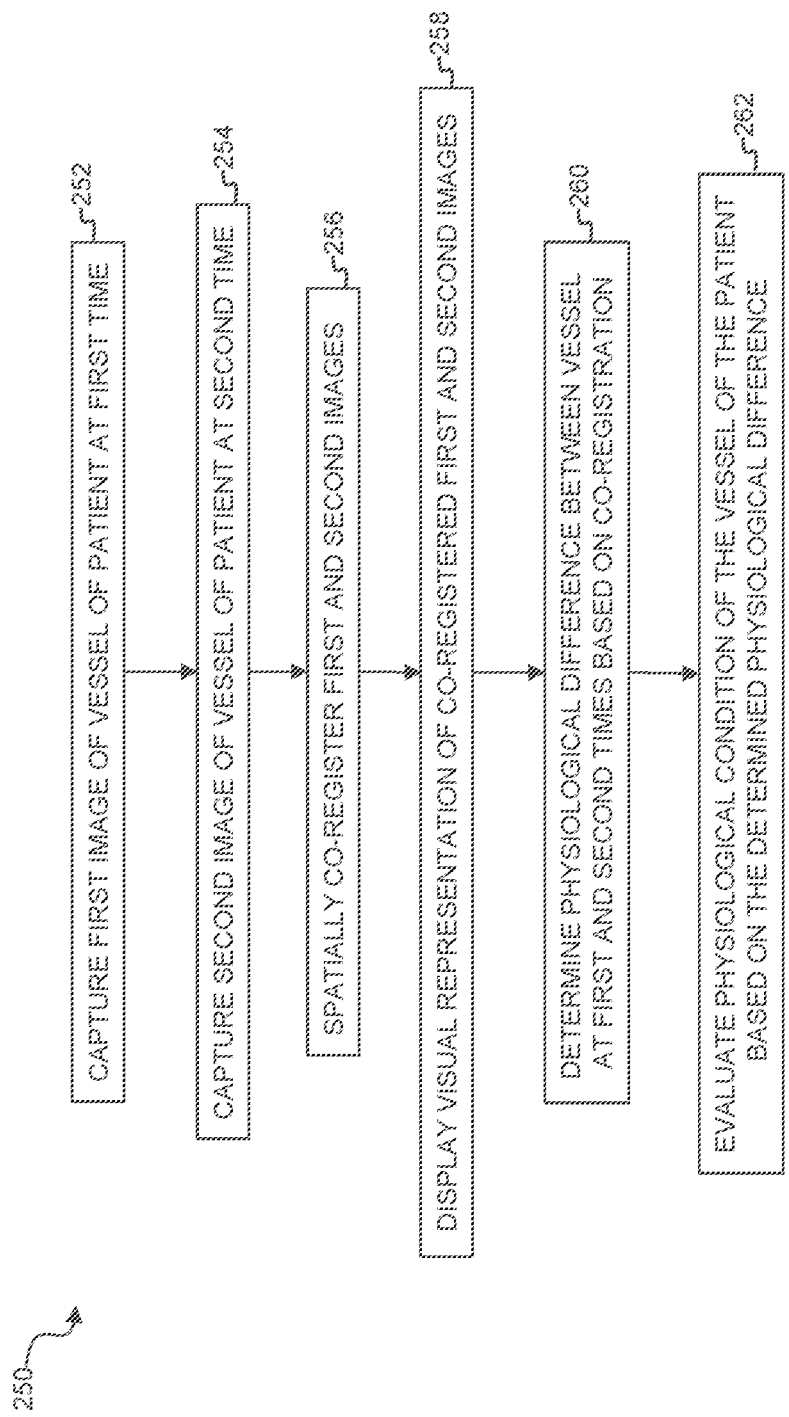
FIG. 9 illustrates a simplified flow chart of a method of assessing the condition of a vessel over time, according to embodiments of the present disclosure.

Referring now to FIG. 9, illustrated is a simplified flow chart of a method 250 of assessing the condition of a vessel over time (i.e., a longitudinal study of a vessel), according to embodiments of the present disclosure. Portions of the method 250 may correspond to the techniques discussed in association with FIGS. 5-8, and may be performed with hardware and/or software components of the processing system 101. Method 250 begins at block 252 where a first graphical diagnostic measurement of a portion of a patient's vasculature is captured at a first time. The portion of a patient's vasculature captured may include an area of interest such as a vessel that includes some type of stenosis. The first graphical diagnostic measurement may be an image associated with any endoluminal or extraluminal imaging modality, such as those described in association with FIGS. 5-8. The point in time at which the first graphical diagnostic measurement is captured may correspond to any point in time in a longitudinal study. The point in time may be before an intravascular procedure is performed, during the course of an intravascular procedure, after an intravascular procedure, or another point in time deemed diagnostically significant. The method 250 then proceeds to block 254 where a second graphical diagnostic measurement of the same portion of the patient's vasculature is captured at a second time subsequent to the first time. In one embodiment, the second graphical diagnostic measurement is an image associated with the same imaging modality as associated with the first graphical diagnostic measurement. In other embodiments, the first and second graphical diagnostic measurements are associated with different imaging modalities. Further, the first and second graphical diagnostic measurements may be captured by one or more imaging instruments and/or imaging systems described in association with FIGS. 1-8. The second point in time may be another point in time in the longitudinal study. In one embodiment, the first point in time is before an intravascular procedure and the second point in time is after the procedure. In other embodiments, the first and second times are both after an intravascular procedure. Alternatively, the longitudinal study is simply designed to monitor a patient's vasculature in the absence of an intravascular procedure.

Next, the method 250 proceeds to block 256 where the first and second graphical diagnostic measurements are spatially co-registered. That is, the image of the patient's vasculature captured at the first time is spatially aligned with the image of the patient's vasculature captured at the second time. The co-registration may be performed according to one or more of the co-registration techniques discussed above or incorporated by reference. In that regard, the processing system 101 may perform the co-registration using co-registration algorithms implemented in hardware and/or software. In one embodiment, spatially co-registering the first and second graphical diagnostic measurements includes overlaying the second graphical diagnostic measurement over the first graphical diagnostic measurement to form a composite image, as discussed in association with FIGS. 6 and 8. One of ordinary skill in the art would recognize that the same techniques may be applied to co-register and overlay more than two graphical diagnostic measurements and form a composite image. In some cases, overlaying more than two graphical diagnostic measurements may allow a practitioner to better evaluate a patient.

The method 250 then continues to block 258 where a visual representation of the co-registered first and second graphical diagnostic measurements is output on a display associated with the processing system 101. In some embodiments, the visual representation is a composite image of the first and second graphical diagnostic measurements, as illustrated in FIGS. 6 and 8. In other embodiments, the visual representation includes the first and second graphical diagnostic measurements arranged in an adjacent manner with the area of interest in the first and second graphical diagnostic measurements located in the same relative position in each of the images. Then, at block 260, it is determined whether there is a physiological difference between the portion of the patient's vasculature at the first time and at the second time based on the co-registration of the first and second graphical diagnostic measurements. In one embodiment, a practitioner visually inspects the visual representation of the co-registered first and second graphical diagnostic measurements to make such a determination. In other embodiments, the processing system 101 automatically makes the determination using diagnostic algorithms that analyze the first and second graphical diagnostic measurements. In that regard, after an automated determination, the processing system 101 may output a textual and/or graphical report highlighting any changes in the physiological condition of the vessel for consideration by a practitioner.

Finally, the method 250 ends at block 262, where the physiological condition of the patient's vasculature is evaluated based on the determined physiological difference. In some embodiments, this evaluation may include determining whether a blood flow through a vessel has improved between the point in time the first graphical diagnostic measurement was captured and the point in time the second graphical diagnostic measurement was captured. In that regard, such an evaluation of the physiological condition of the patient's vasculature may be part of a longitudinal study to measure the effectiveness of an intravascular procedure, such as the placement of a stent within a lumen, the effectiveness of a non-invasive procedure, such as the administration of a drug, or the effectiveness of a combination of an invasive and a non-invasive procedure. In some embodiments, the evaluation in block 262 may be performed by the processing system 101 with hardware and/or software-based evaluation algorithms that analyze the determined physiological difference and provide a human-readable evaluation of the patient's vessel.

In this manner, the method 250 displays co-registered image data collected during the course of a longitudinal study for use by a practitioner in evaluating a patient. Because such image data has been spatially co-registered, a practitioner may efficiently evaluate the condition of a patient over time in a visual manner, which may lead to more accurate diagnoses than evaluations based on numerical measurements alone.

It should be recognized that the method 250 of assessing the condition of a vessel over time may include different and/or additional steps, and that one or more of the illustrated blocks may be performed in a different order. Examples of the anatomical structure to which the aforementioned co-registration of graphical diagnostic images captured over time may be applied include a coronary vessel, a coronary lesion, a vessel, a vascular lesion, a lumen, a luminal lesion, and/or a valve. One of ordinary skill in the art would recognize that the techniques of method 250 may be applied to lumens of a subject's body other than blood vessels (for example, a lumen of the gastrointestinal or respiratory tract). Additionally, any number of graphical diagnostic measurements may be utilized during the course of method 250 to assess the condition of a vessel or other lumen.

Figure 10:
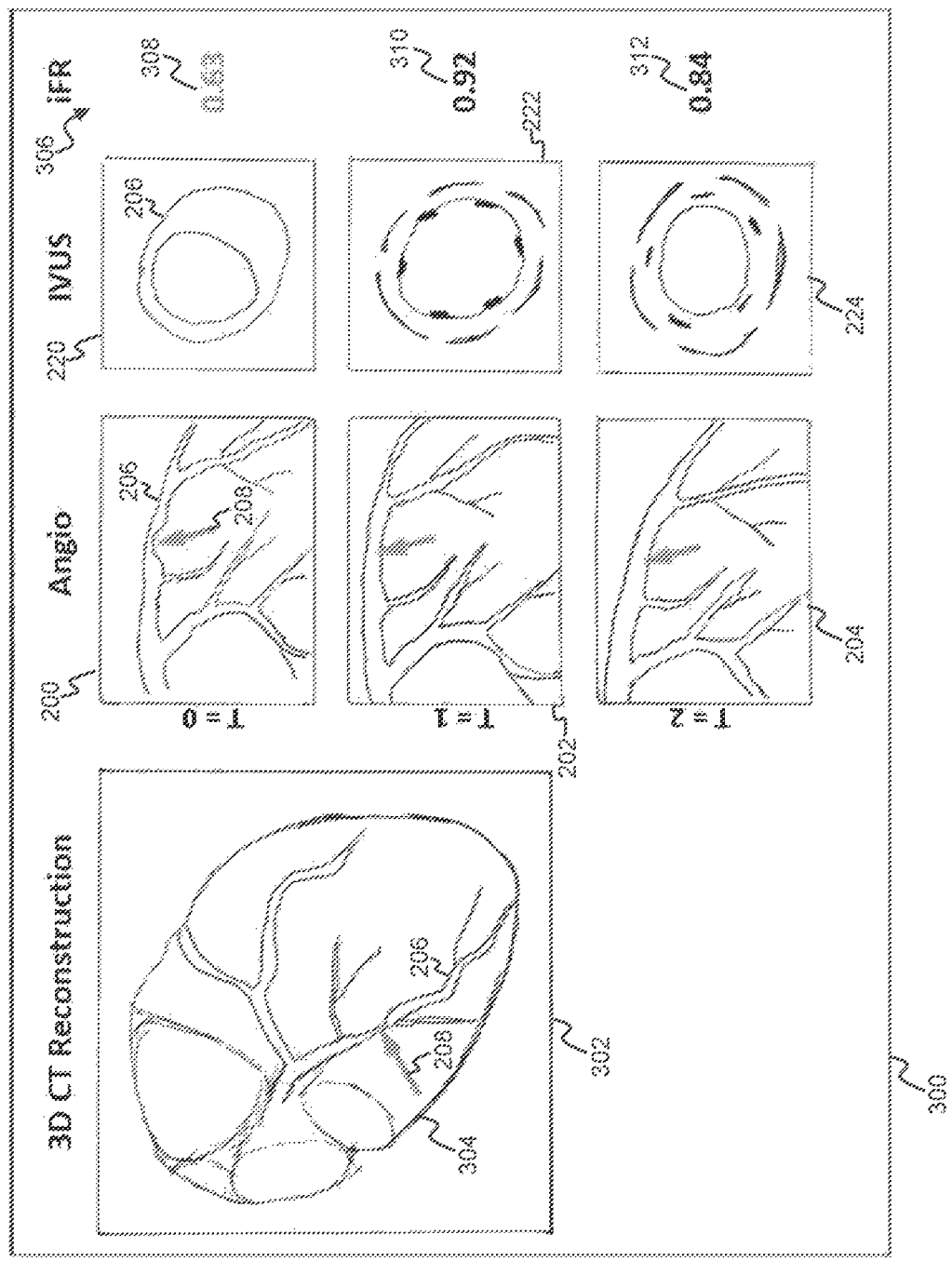
FIG. 10 illustrates a graphical user interface (GUI) screen configured to facilitate the multi-modality assessment of a patient's vasculature over time, according to aspects of the present disclosure.

Referring now to FIG. 10, illustrated is a graphical user interface (GUI) screen 300 configured to facilitate the multi-modality assessment of a patient's vasculature over time, according to aspects of the present disclosure. Specifically, the GUI screen 300 includes a plurality of stylized images of a portion of a patient's vasculature captured at different points in time and with multiple different imaging modalities. One of ordinary skill in the art will recognize that the images illustrated in FIG. 10 are simply examples, and the intravascular elements depicted may correspond to any blood vessel—coronary, systemic, pulmonary, or otherwise—in a patient. Further, the GUI screen 300 may be displayed on a display of a system assessing a patient's vasculature, such as display 118 and/or display 122 associated with the processing system 101 (FIGS. 1, 4). That is, one or more components (e.g., a processor, processing circuit, and/or dedicated graphics processor, etc.) of the system 101 may cause the display of the GUI screen 300.

In more detail, the GUI screen 300 includes a three-dimensional CT reconstruction 302 of a patient's heart 304. In the illustrated embodiment, the heart 304 includes the vessel 206 illustrated in FIGS. 5-8. In some embodiments, the three-dimensional CT reconstruction 302 may be rotated about a vertical axis, a horizontal axis, or an arbitrarily-chosen axis. In some implementations, the three dimensional model is displayed adjacent to a corresponding two dimensional depiction of the vessel. In that regard, the GUI screen 300 also includes the extraluminal images 200, 202, and 204 previously illustrated in FIG. 5 and the endoluminal images 220, 222, and 224 previously illustrated in FIG. 7. Notably, the extraluminal images 200, 202, and 204 are images associated with a different imaging modality than the endoluminal images 220, 222, and 224. For instance, the extraluminal images 200, 202, and 204 may be angiographic images captured by the external imaging system 117, and the endoluminal images 220, 222, and 224 may be IVUS images captured by any of the catheter-based instruments 108, 110,130, 132, 152, and 175 discussed above. The GUI screen 300 also includes a plurality of numerical measurements 306 associated with the portion of the patient's vasculature captured in the adjacent extraluminal and endoluminal images. The numerical measurements 306 were taken at the same points in time as the extraluminal and endoluminal images (i.e., time 0, time 1, and time 2). In the illustrated embodiment, the numerical measurements 306 are iFR calculations (as described, for example, in U.S. patent application Ser. No. 13/460,296, filed Apr. 30, 2012, which is hereby incorporated by reference in its entirety) associated with a stenosis in the vessel 206, but, in alternative embodiments, they may be other types of numerical measurements related to pressure and/or flow of blood through a vessel such as FFR, CFR, or BSR measurements.

In the GUI screen 300, extraluminal images 200, 202, and 204 have been spatially co-registered such they depict the same portion of the patient's vasculature over time. Similarly, endoluminal images 220, 222, and 224 have been spatially co-registered such they depict the same portion of the patient's vessel 206 over time.

Additionally, the extraluminal image 200 captured at time 0 is positioned adjacent to the endoluminal image 220 also captured at time 0. In that regard, the extraluminal image 200 has been spatially and temporally co-registered with the endoluminal image 220 so that the images depict the same portion of the patient's vasculature at the same time (i.e. at time 0). In this case, the images 200 and 220 both depict the area of interest in the vessel 206 that includes a stenosis, as described above. Further, as shown in FIG. 10, a numerical measurement 308 is positioned adjacent the images 200 and 220. In that regard, the numerical measurement 308 has been spatially and temporally co-registered with the images 200 and 220, such that the numerical measurement 308 corresponds to the state of the vessel 206 at the time the images 200 and 220 were captured. Similarly, extraluminal image 202 captured at time 1 is positioned adjacent to the endoluminal image 222 also captured at time 1. In that regard, the extraluminal image 202 has been spatially and temporally co-registered with the endoluminal image 222 so that the images depict the same portion of the patient's vasculature at the same time. Further, a numerical measurement 310 adjacent the images 202 and 222 has been spatially and temporally co-registered with the images, such that the numerical measurement corresponds to the state of the vessel 206 as shown in the images 202 and 222. Similarly, images 204 and 224 and a numerical measurement 312 have been spatially and temporally co-registered.

In this manner, the GUI screen 300 displays co-registered multi-modality data collected during the course of one or more longitudinal studies. Because such multi-modality image data has been spatially and temporally co-registered, a practitioner may efficiently evaluate the condition of a patient over time in a visual manner, which may lead to more accurate diagnoses than evaluations based on numerical measurements alone.

Further, in the example embodiment of FIG. 10, the extraluminal images 200, 202, and 204 and endoluminal images 220, 222, and 224 have been spatially co-registered with the three-dimensional CT reconstruction 302. In that regard, a practitioner may select an area of interest with the arrow 208 and all available diagnostic data corresponding to the selected area is displayed in the GUI screen 300. In the illustrated example, the portion of the vessel 206 selected by the arrow 208 in the three-dimensional CT reconstruction 302 has been imaged using angiographic and IVUS techniques over the course of a longitudinal study spanning time 0 to time 2. An iFR, FFR, or other pressure-based longitudinal study corresponding to the area of interest in vessel 206 is also available and thus displayed in GUI screen 300. In one embodiment, the user may select both the type of depiction(s) (two dimensional (including imaging modality type) and/or three dimensional) along with what visualization mode(s) and/or portions thereof will be utilized. The system will output a corresponding display based on the user's preferences/selections and/or system defaults. In some embodiments, two-dimensional image data may include multiple views about a vertical axis such that different two-dimensional views are shown when the three-dimensional CT reconstruction 302 is rotated. While the visual representations of FIG. 10 have been described in the context of a single GUI screen 300, it is understood that a system may display any combination of these visual representations in series, simultaneously, and/or combinations thereof. In some instances, a system provides the user the ability to select which individual visual representation and/or combination of visual representations will be displayed.

One of ordinary skill in the art would recognize that the GUI screen 300 is simply an example and that such user interface screens may include additional and/or different graphical and textual components and control elements. For instance, the GUI screen 300 may also include composite diagnostic images generated from two or more endoluminal or extraluminal images captured over time, such as the composite images 210 and 230 respectively illustrated in FIGS. 6 and 8. Such composite images may allow a practitioner to more effectively identify changes in a patient's physiology over time. Additionally, one of ordinary skill in the art would recognize that although three endoluminal images and three extraluminal images have been co-registered on the GUI screen 300, the same techniques may be applied to any number of endoluminal and/or extraluminal images. In some cases, displaying more than three images of each type may allow a practitioner to better evaluate a patient.

Figure 11:
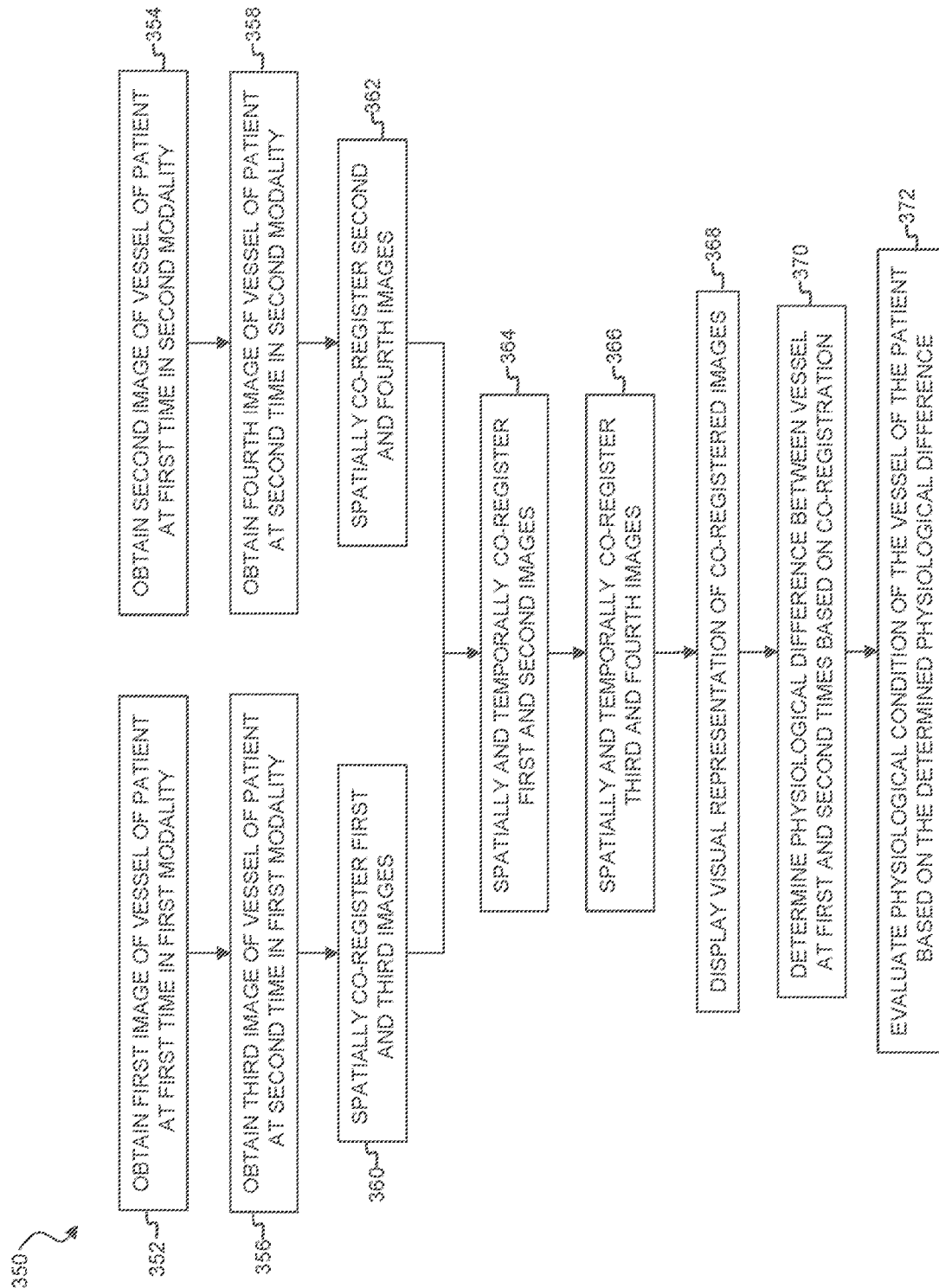
FIG. 11 illustrates a simplified flow chart of a method for assessing the condition of a vessel over time, according to another embodiment of the present disclosure.

Referring now to FIG. 11, illustrated is a simplified flow chart of a method 350 for assessing the condition of a vessel over time (i.e., a longitudinal study of a vessel), according to embodiments of the present disclosure. Portions of the method 350 may correspond to the techniques discussed in association with FIGS. 5-8 and 10, and may be performed with hardware and/or software components of the processing system 101. Method 350 begins at blocks 352 and 354 where first and second graphical diagnostic measurements of a portion of a patient's vasculature are captured at a first time. The portion of the patient's vasculature captured may include an area of interest such as a vessel that includes some type of stenosis. The first and second graphical diagnostic measurements may be images associated with different imaging modalities. In one embodiment, the first graphical diagnostic measurement may be an image associated with an endoluminal imaging modality—such as IVUS, OCT, IVPA, intravascular MRI, thermal, ICE, TEE, TTE and/or other internal imaging techniques—and the second graphical diagnostic measurement may be an image associated with an extraluminal imaging modality, such as x-ray, angiogram, CT, PET, PET-CT, MRI, SPECT, and/or other external-based imaging modality. Further, the first and second graphical diagnostic measurements may be captured by one or more imaging instruments and/or imaging systems described in association with FIGS. 1-8. The point in time at which the first and second graphical diagnostic measurements are captured may correspond to any point in time in a longitudinal study. The point in time may be before an intravascular procedure is performed, during the course of an intravascular procedure, after an intravascular procedure, or another point in time deemed diagnostically significant. Note that, in some embodiments, the "point in time" at which the first and second graphical diagnostic measurements are captured may refer to a non-instantaneous block of time. That is, a diagnostically-insignificant amount of time may transpire between the capture of the first image and the capture of the second image in blocks 352 and 354. In one example, the first and second images may be captured sequentially during a diagnostic session.

The method 350 continues to blocks 356 and 358 where third and fourth graphical diagnostic measurements of the same portion of the patient's vasculature is captured at a second time subsequent to the first time. The third graphical diagnostic measurement is an image associated with the same imaging modality as associated with the first graphical diagnostic measurement, but may be captured with the same or a different instrument. Similarly, the fourth graphical diagnostic measurement is an image associated with the same imaging modality as associated with the second graphical diagnostic measurement, but may be captured with the same or a different instrument. Further, the third and fourth graphical diagnostic measurements may be captured by one or more imaging instruments and/or imaging systems described in association with FIGS. 1-8. The second point in time may be another point in time in the longitudinal study. In one embodiment, the first time is before an intravascular procedure and the second time is after the procedure. In other embodiments, the first and second times are both after an intravascular procedure. Alternatively, the longitudinal study is simply designed to monitor a patient's vasculature in the absence of an intravascular procedure. Note that, in some embodiments, the "point in time" at which the third and fourth graphical diagnostic measurements are captured may refer to a non-instantaneous block of time. That is, a diagnostically-insignificant amount of time may transpire between the capture of the third image and the capture of the fourth image in blocks 356 and 358. In one example, the third and fourth images may be captured sequentially during a diagnostic session.

Next, in block 360, the first and third graphical diagnostic measurements are spatially co-registered. That is, the image of the patient's vasculature captured at the first time in the first modality is spatially aligned with the image of the patient's vasculature captured at the second time in the same modality. In one embodiment, spatially co-registering the first and third graphical diagnostic measurements includes overlaying the third graphical diagnostic measurement over the first graphical diagnostic measurement to form a composite image, as discussed in association with FIGS. 6 and 8. Similarly, in block 362, the second and fourth graphical diagnostic measurements are spatially co-registered. That is, the image of the patient's vasculature captured at the first time in the second modality is spatially aligned with the image of the patient's vasculature captured at the second time in the same modality. In one embodiment, spatially co-registering the second and fourth graphical diagnostic measurements includes overlaying the fourth graphical diagnostic measurement over the second graphical diagnostic measurement to form a composite image, as discussed in association with FIGS. 6 and 8. The co-registration in blocks 360 and 362 may be performed according to one or more of the co-registration techniques described in association with FIGS. 5-9 or incorporated by reference. In one embodiment, the processing system 101 may perform the co-registration using co-registration algorithms implemented in hardware and/or software.

The method 350 next proceeds to block 364 where the first and second graphical diagnostic measurements are spatially and temporally co-registered. In that regard, the image of the patient's vasculature captured at the first time in the first modality is spatially co-registered with the image of the patient's vasculature also captured at the first time but in the second modality. In one embodiment, this spatial so-registration aligns an endoluminal image with an extraluminal image. Further, the temporal co-registration between the first and second graphical diagnostic measurements ensures that the images depict the portion of the patient's vasculature at the same time to enable accurate diagnoses. In block 366, the third and fourth graphical diagnostic measurements are similarly spatially and temporally co-registered. In that regard, the image of the patient's vasculature captured at the second time in the first modality is spatially and temporally aligned with the image of the patient's vasculature also captured at the second time but in the second modality.

The method then continues to block 368 where visual representations of the co-registered first, second, third, and fourth graphical diagnostic measurements are output on a display associated with the processing system 101. In some embodiments, such as GUI screen 300 illustrated in FIG. 10, the visual representations include the first, second, third, and fourth graphical diagnostic measurements arranged in an adjacent manner, where each image depicts the area of interest (e.g., a stenosis in a vessel) in the same relative position to aid diagnosis. In other embodiments, the visual representations include a composite image of the first and third graphical diagnostic measurements (that are in the first modality) and a composite image of the second and fourth graphical diagnostic measurements (that are in the second modality).

Next, at block 370, it is determined whether there is a physiological difference between the portion of the patient's vasculature at the first time and the second time based on the spatial and temporal co-registration of the first, second, third, and fourth graphical diagnostic measurements. In one embodiment, a practitioner visually inspects the visual representations of the spatially co-registered first and third graphical diagnostic measurements, the spatially co-registered second and fourth graphical diagnostic measurements, the spatially and temporally co-registered first and second graphical diagnostic measurements, and spatially and temporally co-registered third and fourth graphical diagnostic measurements to make such a determination. In other embodiments, the processing system 101 automatically makes the determination using diagnostic algorithms that analyze the graphical diagnostic measurements. In that regard, after an automated determination, the processing system 101 may output a textual and/or graphical report highlighting any changes in the physiological condition of the vessel for consideration by a practitioner.

Finally, the method 350 ends at block 372, where the physiological condition of the patient's vasculature is evaluated based on the determined physiological difference. In some embodiments, this evaluation may include determining whether a blood flow thorough a vessel has improved between the point in time the first and second graphical diagnostic measurements were captured and the point in time the third and fourth graphical diagnostic measurements were captured. In that regard, such an evaluation of the physiological condition of the patient's vasculature may be part of a longitudinal study to measure the effectiveness of an intravascular procedure, such as the placement of a stent within a lumen. In some embodiments, the evaluation in block 372 may be performed by the processing system 101 with hardware and/or software-based evaluation algorithms that analyze the determined physiological difference and provide a human-readable evaluation of the patient's vessel.

In this manner, the method 350 displays spatially and temporally co-registered image data collected during the course of a longitudinal study for use by a practitioner in evaluating a patient's physiological condition. Because such image data has been spatially and temporally co-registered, a practitioner may efficiently evaluate the condition of a patient over time in a visual manner, which may lead to more accurate diagnoses than evaluations based on numerical measurements alone.

It should be recognized that the method 350 of assessing the condition of a vessel over time may include different and/or additional steps, and that one or more illustrated blocks may be performed in a different order. For instance, the method 350 may also include blocks related to collecting numerical measurements—such as pressure and flow measurements/calculations—at the each of the first and second times. Such numerical measurements may then be temporally co-registered with the graphical diagnostics measurements, such that determining any physiological difference in the patient is also based on the co-registered numerical measurements. Examples of the anatomical structure to which the aforementioned co-registration of graphical diagnostic images captured over time may be applied include a coronary vessel, a coronary lesion, a vessel, a vascular lesion, a lumen, a luminal lesion, and/or a valve. One of ordinary skill in the art would also recognize that the techniques of method 350 may be applied to lumens of a subject's body other than blood vessels (for example, a lumen of the gastrointestinal or respiratory tract). Additionally, any number of graphical diagnostic measurements may be utilized during the course of method 350 to assess the condition of a vessel or other lumen.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:
a processor configured to:
receive a first image of a blood vessel obtained at a first time, wherein the first image depicts a same location of the blood vessel with a first vessel structure;
receive a second image of the blood vessel obtained at a second time, wherein the second image depicts the same location of the blood vessel with a second vessel structure;
receive a third image of the blood vessel obtained at a third time, wherein the third image depicts the same location of the blood vessel with a third vessel structure;
generate a screen display comprising:
the first image;
the second image; and
the third image; and
output the screen display on a display,
wherein the first image, the second image, and the third image are displayed simultaneously in the screen display,
wherein the first image, the second image, and the third image comprise a same imaging modality,
wherein the first image is obtained before a therapy directed to the same location is performed,
wherein at least one of the second image or the third image is obtained after the therapy directed to the same location is performed,
wherein the therapy comprises at least one of percutaneous coronary intervention (PCI), angioplasty, stenting, coronary artery graft, ablation, cryotherapy, atherectomy, or administration of a drug, and
wherein at least one of the second vessel structure or the third vessel structure is different than the first vessel structure as a result of a physiological change caused by the therapy.

2. The apparatus of claim 1, wherein the screen display further comprises:
a first label proximate to the first image and identifying the first time;
a second label proximate to the second image and identifying the second time;
a third label proximate to the third image and identifying the third time.

3. The apparatus of claim 1,
wherein the second image and the third image are obtained after the therapy is performed, wherein the second vessel structure and the third vessel structure are different than the first vessel structure.

4. The apparatus of claim 3, wherein the third vessel structure is different than the second vessel structure.

5. The apparatus of claim 3,
wherein the second image is obtained during an intravascular procedure to perform the therapy, and
wherein the third image is obtained during a follow-up visit.

6. The apparatus of claim 3,
wherein the second image is obtained during an initial follow-up visit, and
wherein the third image is obtained during a subsequent follow-up visit.

7. The apparatus of claim 1, wherein the first image, the second image, and the third image comprise a same view of the blood vessel.

8. The apparatus of claim 1, wherein the screen display further comprises at least one of:
a first marker overlaid on the first image proximate to the same location such that the same location with the first vessel structure is visually indicated;
a second marker overlaid on the second image proximate to the same location such that the same location with the second vessel structure is visually indicated; or
a third marker overlaid on the third image proximate to the same location such that the same location with the third vessel structure is visually indicated.

9. The apparatus of claim 8,
wherein the first image, the second image, and the third image depict a length of the blood vessel, and
wherein the same location indicated by at least one of the first marker, the second marker, or the third marker is a location along the length of the blood vessel.

10. The apparatus of claim 1, wherein the first image, the second image, and the third image are extraluminal images.

11. The apparatus of claim 10, wherein the first image, the second image, and the third image comprise one of: an x-ray image, an angiogram image, an ultrasound image, a two-dimensional computed tomography (CT) image, a three-dimensional CT image, a computed tomography angiogram (CTA) image, a positron emission tomography (PET) image, a PET-CT image, a magnetic resonance image (MRI), or a single-photon emission computed tomography (SPECT) image.

12. The apparatus of claim 1, wherein the first image, the second image, and the third image are endoluminal images.

13. The apparatus of claim 12, wherein the first image, the second image, and the third image comprise one of: an intravascular ultrasound (IVUS) image, a forward looking IVUS (FL-IVUS) image, an intravascular photoacoustic (IVPA) image, a near-infrared Spectroscopy (NIRS) image, an optical coherence tomography (OCT) image, an intracardiac echocardiography (ICE) image, a forward-looking ICE (FLICE) image, or an intravascular magnetic resonance image (MRI).

14. The apparatus of claim 1, further comprising an imaging device configured to obtain at least one of the first image, the second image, or the third image.

15. The apparatus of claim 14, wherein the imaging device comprises an extraluminal imaging device.

16. The apparatus of claim 14, wherein the imaging device comprises an endoluminal imaging device.

17. The apparatus of claim 1,
wherein the processor is further configured to:
obtain a first pressure ratio at the first time and corresponding to the first vessel structure;
obtain a second pressure ratio at the second time and corresponding to the second vessel structure; and
obtain a third pressure ratio at the third time and corresponding to the third vessel structure, and
wherein the screen display further comprises:
a first representation of the first pressure ratio proximate to the first image;
a second representation of the second pressure ratio proximate to the second image; and
a third representation of the third pressure ratio proximate to the third image.

* * * * *